(12) United States Patent
Sprinkle (10) Patent No.: US 11,452,561 B2
(45) Date of Patent: *Sep. 27, 2022

(54) TISSUE ABLATION CANNULA ASSEMBLY

(71) Applicant: Stryker Corporation, Kalamazoo, MI (US)

(72) Inventor: Thomas Sprinkle, Kalamazoo, MI (US)

(73) Assignee: Stryker Corporation, Kalamazoo, MI (US)

( * ) Notice: Subject to any disclaimer, the term of this patent is extended or adjusted under 35 U.S.C. 154(b) by 1029 days.

This patent is subject to a terminal disclaimer.

(21) Appl. No.: 16/151,989

(22) Filed: Oct. 4, 2018

(65) Prior Publication Data

US 2019/0029748 A1    Jan. 31, 2019

Related U.S. Application Data

(63) Continuation of application No. 15/898,820, filed on Feb. 19, 2018, now Pat. No. 10,159,526, which is a
(Continued)

(51) Int. Cl.
*A61B 18/14*    (2006.01)
*A61B 18/00*    (2006.01)
(Continued)

(52) U.S. Cl.
CPC ........ *A61B 18/1477* (2013.01); *A61B 18/148* (2013.01); *A61B 2018/00791* (2013.01);
(Continued)

(58) Field of Classification Search
CPC .............. A61B 18/1477; A61B 18/148; A61B 18/1482; A61B 18/1487;
(Continued)

(56) References Cited

U.S. PATENT DOCUMENTS 4,699,616 A    10/1987    Nowak et al.
5,069,206 A    12/1991    Crosbie
(Continued)

FOREIGN PATENT DOCUMENTS

DE    3838840 A1    5/1990
EP    1056403 B1    1/2005
(Continued)

OTHER PUBLICATIONS

English language abstract and machine-assisted English translation for DE 38 38 840 extracted from espacenet.com database on Jan. 3, 2018, 16 pages.
(Continued)

*Primary Examiner* — Thomas A Giuliani
(74) *Attorney, Agent, or Firm* — Howard & Howard Attorneys PLLC (57) ABSTRACT

An assembly for radiofrequency ablation of tissue. A cannula includes a cannula hub and a cannula body including a cannula bend, a lumen, and side opening within an outer side of the cannula bend. An electrode includes an electrode hub and an electrode body dimensioned to be inserted within the lumen of the cannula body in at least first and second rotational orientations as indicated by registration of respective indicia on the cannula and electrode hubs. A distal section of the electrode body extends past the side opening of the cannula body in the first rotational orientation, and the distal section extends through the side opening in the second rotational orientation. The indicia of the cannula hub and the electrode hub may be indicative of the orientation of the cannula bend and an electrode bend, respectively. Methods of performing radiofrequency ablation of the tissue with the assembly are also disclosed.

17 Claims, 5 Drawing Sheets

Related U.S. Application Data continuation of application No. 14/824,673, filed on Aug. 12, 2015, now abandoned, which is a continuation of application No. PCT/US2013/027038, filed on Feb. 21, 2013.

(51) Int. Cl.
*A61B 18/12* (2006.01)
*A61B 90/00* (2016.01)

(52) U.S. Cl.
CPC ............ *A61B 2018/00821* (2013.01); *A61B 2018/124* (2013.01); *A61B 2018/1475* (2013.01); *A61B 2090/0807* (2016.02); *A61B 2090/0811* (2016.02)

(58) Field of Classification Search
CPC .... A61B 2018/1465; A61B 2018/1475; A61B 2018/162; A61B 2018/1253; A61B 2018/126; A61B 2018/00916; A61B 2018/00958; A61B 2090/0807; A61B 2090/0811
USPC ........ 606/41, 44–50; 607/99, 101, 113, 116; 604/21, 22, 264
See application file for complete search history.

(56) References Cited

U.S. PATENT DOCUMENTS

| | | |
|---|---|---|
| 5,106,376 A | 4/1992 | Mononen et al. |
| 5,213,578 A * | 5/1993 | Heiliger ............ A61B 17/3401 604/164.11 |
| 5,263,939 A | 11/1993 | Wortrich |
| 5,433,739 A | 7/1995 | Sluijter et al. |
| 5,458,597 A | 10/1995 | Edwards et al. |
| 5,472,441 A | 12/1995 | Edwards et al. |
| 5,507,743 A | 4/1996 | Edwards et al. |
| 5,536,267 A | 7/1996 | Edwards et al. |
| 5,599,345 A | 2/1997 | Edwards et al. |
| 5,599,346 A | 2/1997 | Edwards et al. |
| 5,645,566 A | 7/1997 | Brenneman et al. |
| 5,672,173 A | 9/1997 | Gough et al. |
| 5,672,174 A | 9/1997 | Gough et al. |
| 5,683,384 A | 11/1997 | Gough et al. |
| 5,728,143 A | 3/1998 | Gough et al. |
| 5,735,847 A | 4/1998 | Gough et al. |
| 5,782,827 A | 7/1998 | Gough et al. |
| 5,800,484 A | 9/1998 | Gough et al. |
| 5,810,804 A | 9/1998 | Gough et al. |
| 5,863,290 A | 1/1999 | Gough et al. |
| 5,913,855 A | 6/1999 | Gough et al. |
| 5,925,042 A | 7/1999 | Gough et al. |
| 5,928,229 A | 7/1999 | Gough et al. |
| 5,935,123 A | 8/1999 | Edwards et al. |
| 5,951,547 A | 9/1999 | Gough et al. |
| 5,980,517 A | 11/1999 | Gough |
| 6,053,937 A | 4/2000 | Edwards et al. |
| 6,059,780 A | 5/2000 | Gough et al. |
| 6,071,280 A | 6/2000 | Edwards et al. |
| 6,080,150 A | 6/2000 | Gough |
| 6,090,105 A | 7/2000 | Zepeda et al. |
| 6,132,425 A | 10/2000 | Gough |
| 6,235,023 B1 | 5/2001 | Lee et al. |
| 6,330,478 B1 | 12/2001 | Lee et al. |
| 6,471,698 B1 | 10/2002 | Edwards et al. |
| 6,500,175 B1 | 12/2002 | Gough et al. |
| 6,551,311 B2 | 4/2003 | Lee et al. |
| 6,569,159 B1 | 5/2003 | Edwards et al. |
| 6,605,085 B1 | 8/2003 | Edwards |
| 6,632,221 B1 | 10/2003 | Edwards et al. |
| 6,632,222 B1 | 10/2003 | Edwards et al. |
| 6,641,580 B1 | 11/2003 | Edwards et al. |
| 6,652,516 B1 | 11/2003 | Gough |
| 6,660,002 B1 | 12/2003 | Edwards et al. |
| 6,663,624 B2 | 12/2003 | Edwards et al. |
| 6,958,062 B1 | 10/2005 | Gough et al. |
| 7,150,744 B2 | 12/2006 | Edwards et al. |
| 7,862,563 B1 | 1/2011 | Cosman et al. |
| 9,517,047 B2 | 12/2016 | Grossman |
| 10,159,526 B2 * | 12/2018 | Sprinkle ............ A61B 18/1477 |
| 2005/0267553 A1 | 12/2005 | Staunton et al. |
| 2005/0277918 A1 * | 12/2005 | Shah .................. A61B 18/1477 606/41 |
| 2006/0084965 A1 * | 4/2006 | Young .................. A61B 18/148 606/41 |
| 2007/0016185 A1 | 1/2007 | Tullis et al. |
| 2007/0179380 A1 | 8/2007 | Grossman |
| 2008/0078806 A1 | 4/2008 | Omaits et al. |
| 2009/0105775 A1 | 4/2009 | Mitchell et al. |
| 2010/0010449 A1 | 1/2010 | Leibowitz et al. |
| 2011/0077644 A1 | 3/2011 | Pham et al. |
| 2011/0213356 A1 | 9/2011 | Wright et al. |
| 2011/0288540 A1 | 11/2011 | Wright et al. |
| 2013/0006232 A1 | 1/2013 | Pellegrino et al. |
| 2015/0342668 A1 * | 12/2015 | Sprinkle .............. A61B 18/148 606/41 |
| 2017/0065334 A1 | 3/2017 | Wright et al. |
| 2018/0168719 A1 | 6/2018 | Sprinkle |

FOREIGN PATENT DOCUMENTS

| | | |
|---|---|---|
| JP | 2009526554 A | 7/2009 |
| JP | 2013526940 A | 6/2013 |
| WO | 0025669 A1 | 5/2000 |

OTHER PUBLICATIONS

English language abstract not found for JP 2009-526554; however, see English language equivalent U.S. Pat. No. 9,517,047. Original document extracted from espacenet.com database on Dec. 21, 2017, 15 pages.

English language abstract not found for JP 2013-526940; however, see English language equivalent U.S. 2017/0065334. Original document extracted from espacenet.com database on Dec. 21, 2017, 70 pages.

Fischer, F.L., Technical Description—cTC Electrode for Cordotomie and DREZ-Tomy, pre-Aug. 12, 2014, pp. 1-9.

PCT "International Search Report and Written Opinion" for PCT/US2013/027038, dated Dec. 2013.

\* cited by examiner

TISSUE ABLATION CANNULA ASSEMBLY

CROSS REFERENCE TO RELATED APPLICATIONS

This is a continuation of U.S. application Ser. No. 15/898,820, filed Feb. 19, 2018, now U.S. Pat. No. 10,159,526, which is a continuation of U.S. application Ser. No. 14/824,673, filed Aug. 12, 2015, now abandoned, which is a continuation of International Application No. PCT/US2013/027038, filed Feb. 21, 2013, each of which is hereby incorporated by reference in its entirety.

FIELD OF THE INVENTION

This invention generally relates to a cannula and electrode assembly used for tissue ablation. The cannula and electrode assembly of this invention has plural conduct tips and be selectively operated so that at any given time a single tips or the plural tips are active.

BACKGROUND OF THE INVENTION

An electrosurgical tool system, often referred to as an electrosurgical system, is a set of components used to flow current through a patient to accomplish a specific medical procedure. Often the procedure is to ablate at least some of the tissue through which the current is flowed to accomplish a desirable therapeutic effect. For example, an electrosurgical procedure is sometimes performed to selectively remove nerve tissue. This may be desirable if a set of the patient's nerves continually transmit signals to the brain that inaccurately indicate that a portion of the patient's body is in appreciable pain. If the receipt of these pain signals adversely affects the quality of life for the patient, an electrosurgical system is employed to ablate the nerves responsible for the transmission of these signals. As a consequence of the tissue ablation process the nerve becomes a lesion. As a result of the nerve becoming a lesion, the nerve no longer transmits pain signals to the brain.

Many electrosurgical systems include a cannula and electrode assembly. As implied by its name this assembly includes a cannula and an electrode. The cannula is a needle like structure with sufficient strength to puncture the skin of the patient and be positioned adjacent the tissue through which the current is to be flowed. The distal end or tip of the cannula is conductive. The electrode is a closed end tube formed of conductive material. The tube is designed to seat in the lumen that extends through the cannula. Owing to the relatively small diameter of the electrode, often 0.4 mm or less in diameter, this tube tends to be relatively fragile. A hub or terminal is connected to the proximal end of the electrode body.

When this type of assembly is used to remove tissue, the cannula is typically initially inserted into the patient and directed to a location adjacent the target tissue, the tissue that is to be removed. During the insertion process a stylet may be seated in the cannula lumen to provide structural strength to the cannula. Once the cannula is in the generally vicinity of the target tissue, the stylet is removed. The electrode is inserted into the cannula lumen. A cable connects the electrode to a control console, also part of the electrosurgical system. The control console functions as the power source that applies current to the electrode. An electrically conductive ground pad, another component of the electrosurgical system, is placed against the patient. The ground pad is also connected to the control console.

The electrode assembly is used by sourcing a current from the control console to the electrode. Since the electrode and cannula physically abut, there is current flow to the cannula. An electrical path is established through the patient from the electrode and sleeve section of the cannula to the ground pad. This current flow is densest through the tissue immediately adjacent the distal end of electrode and the exposed distal end of the cannula. This current flow heats the tissue to a temperature that results in the ablation of the tissue.

Available cannula and electrode assemblies have proven to be good instruments for removing selected sections of tissue. Nevertheless, a limiting characteristic with the use of some of these assemblies is that, when activated, they tend to ablate relatively small volumes of tissue, tissue having a volume of 0.8 $cm^3$ or less. This is especially true of assemblies having cannula with outer diameters of 18 gage or more (1.25 mm or less.) There are procedures in which the practitioner wants to ablate larger sections of tissue than can be removed in a single actuation of the assemblies. Consequently, after a first section of tissue is removed, the practitioner has to reposition the electrode assembly to remove an adjacent section of tissue. This requires the practitioner to, ever so slightly, reposition the electrode array so that, in the next actuation, current is only flowed through the tissue that is to be removed and not flowed through the adjacent tissue that should not be subjected to the removal process. Having to so reposition the electrode assembly, in addition to requiring a significant amount of skill, can lengthen the overall amount of time it takes to perform the procedure.

An alternative cannula-and-electrode assembly has been proposed that is intended to increase the volume of tissue that can be removed with a single placement of the cannula. Specifically, it has been proposed to form the cannula of this type of assembly with a side opening that is located a short distance rearward of the distal end of the cannula. The assembly is further constructed with a means to turn the electrode as it is inserted in the cannula so that the distal end tip of the electrode extends out of this side port. The assembly thus has two tips: the distal end tip of the cannula; and the distal end tip of the electrode. When current is sourced to the assembly, the current flows from these two spaced apart tips.

Consequently, when current is sourced out of the electrode assembly of this invention, a relative dense electric field appears in the area around both of the tips. The field extend over a wider volume than the field output by an assembly with a convention electrode-in-the distal end of the cannula construction. The electrode assembly of this invention thus outputs a relatively dense current flow through a volume larger than is output by a conventionally constructed electrode assembly of the same size.

There are procedures though in which the practitioner may not know until after the procedure is started if it is more appropriate to source current through a one tip assembly or a two tip assembly. Similarly, during the procedure, the practitioner may want to initial apply current using first the one tip (or two tip) assembly and then switch to applying current using a two tip (or one tip) assembly. In either of the above situations, the practitioner may find it necessary to interrupt the procedure in order first remove one cathode and electrode assembly and then insert a second assembly. As part of this process, the practitioner needs to take the time to ensure that the second assembly is properly positioned. Having to perform all these steps can increase the complexity of the procedure and the tip it takes to perform the procedure.

SUMMARY OF THE INVENTION

This invention relates to a new and useful cannula and electrode assembly for flowing current through living tissue. The assembly of this invention is designed so that after being inserted into the living being through which the current is to be sourced the assembly can be configured to source current from a single tips or plural spaced apart tips. In many versions of the invention, the assembly can be set to have two active tips.

The cannula of this assembly is formed so as to have a bend immediately proximal to the distal end of the cannula. The cannula has an outlet opening along the outer surface of the section of the cannula in which the bend is formed.

The electrode includes an elastic shaped section proximal to the distal end. More specifically, the electrode is shaped so as to have a length substantially equal to the length of the lumen that extends through the cannula. The electrode is further formed to have a bend in the section formed from elastic material. The bend is formed so as to be at the same general location along the length of the electrode that the bend is formed in the cannula.

A hub is attached to the proximal end of the electrode. The hub is connected to a cable through which current is sourced to the cannula. In many, but not all versions of the invention, the hub is provided with an indicia that provides an indication of the rotational orientation of the electrode within the cannula.

The assembly of this invention is used by first inserting the cannula in the patient. The cannula is positioned so the distal end tip is located adjacent the tissue through which the current is to be flowed. The electrode is then inserted in the cannula. If the practitioner only wants to flow current out of a single tip, the tip of the cannula, the electrode is inserted in the cannula in the rotational orientation so that the bend in the electrode is in same orientation as the bend in the cannula. Consequently, when the electrode is seated in the cannula, the tip of the electrode is seated in the distal end of the lumen of the cannula. Current is therefore sourced only from the tip of the cannula.

Alternatively, the practitioner can configure the assembly of this invention so that current can be simultaneously sourced from two tips. The assembly is so positioned by setting the rotational orientation of the electrode so that it is out of orientation with the bend in the cannula. When the electrode, in this orientation, is inserted in the cannula, the distal end of the electrode will extend out of the side port of the cannula. Thus while embedded in the patient, the assembly in this configuration has two active tips; the cannula tip and the electrode tip. As a consequence of the application of current to the electrode, current is flowed from both tips through the adjacent tissue.

BRIEF DESCRIPTION OF THE DRAWINGS

The invention is pointed out with particularity in the claims. The above and further features and advantages of this invention are understood by reference to the following Detailed Description taken in conjunction with the accompanying drawings in which

DETAILED DESCRIPTION

Figure 1:
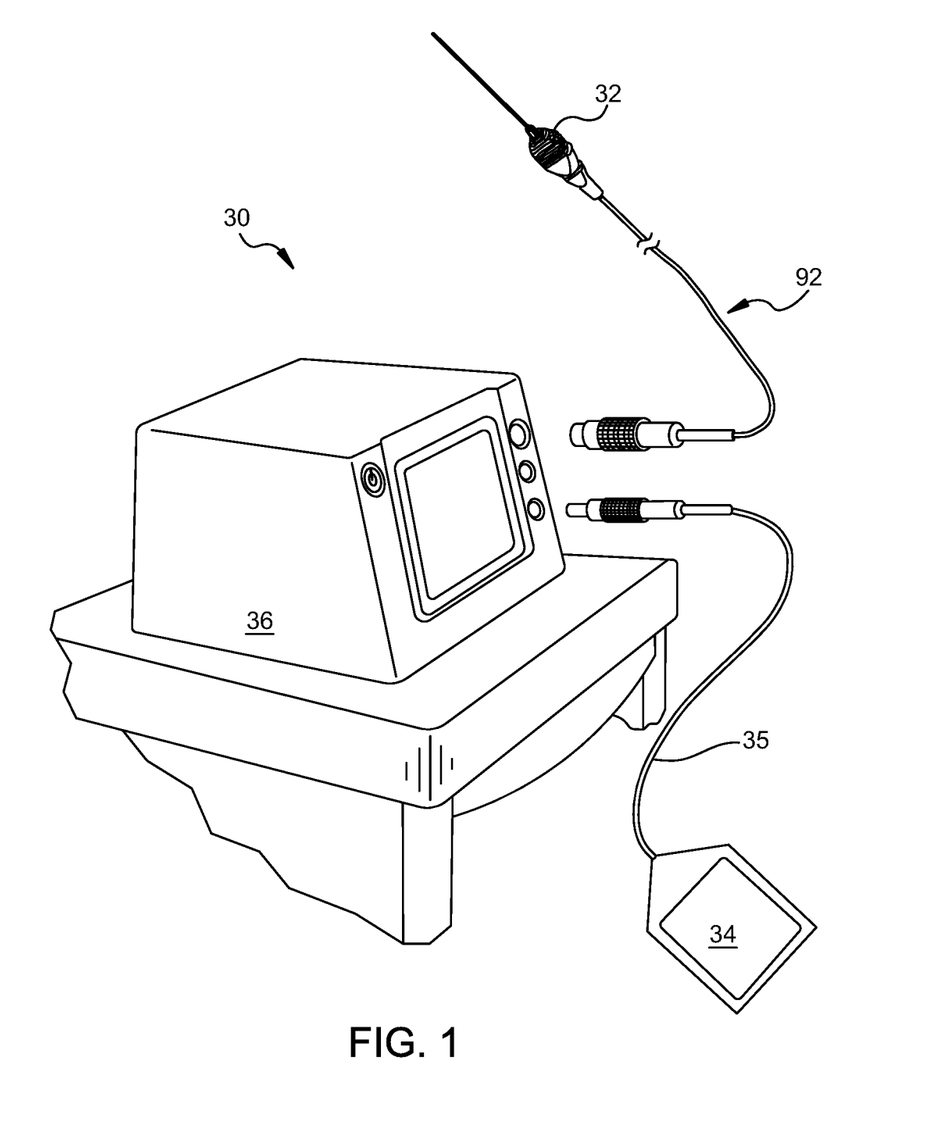
FIG. 1 depicts an electrosurgical system with a cannula and electrode assembly of this invention.

FIG. 1 illustrates an electrosurgical system 30 including a cannula and electrode assembly 32 of this invention. System 30 also includes a ground pad 34 and a control console 36. Both the cannula and electrode assembly 32 and ground pad 34 are connected to the control console 36. The control console 36 functions a power source that sources a current for flow between the cannula and electrode assembly 32 and the ground pad 34

Figure 2:
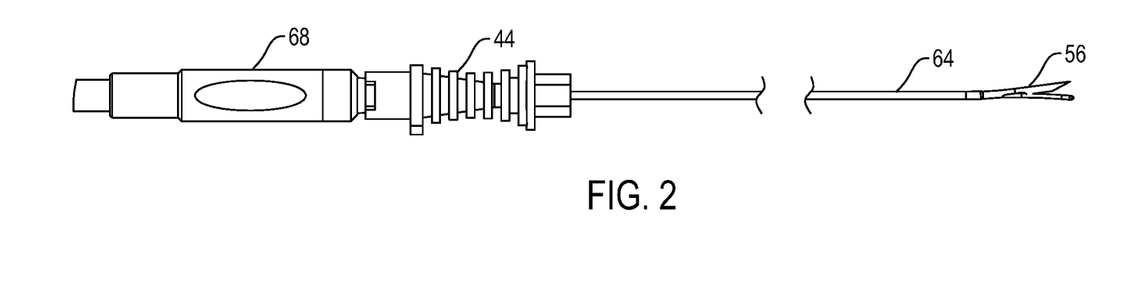
FIG. 2 is a plan view of the cannula and electrode assembly of this invention.
Figure 3:
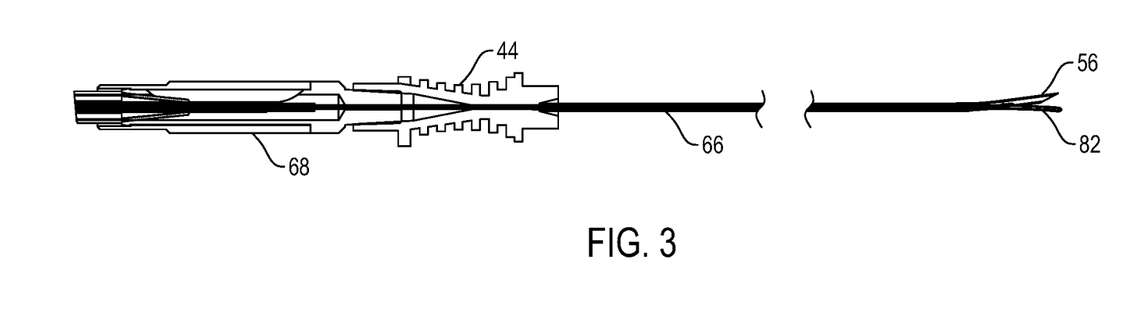
FIG. 3 is a cross sectional view of the cannula and electrode assembly of FIG. 2.

The cannula and the cannula and electrode assembly 32, as seen in FIGS. 2 and 3 includes a cannula 42 and an electrode 66. Electrode 66 is disposed in the cannula 42. FIGS. 2 and 3 depict one operating configuration of assembly 32, wherein the distal end tip of the electrode 62 is located outside of the cannula 42.

Figure 4:
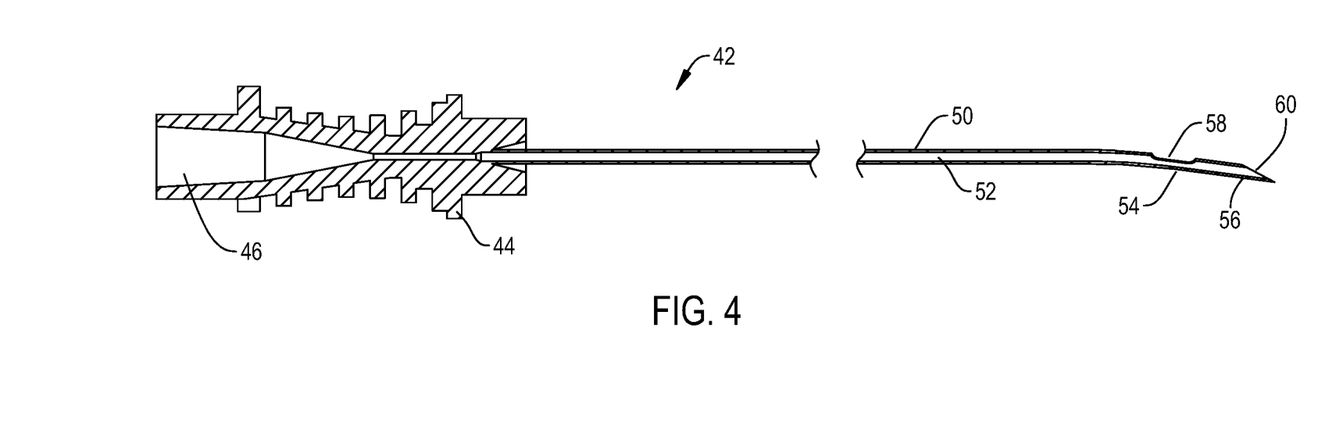
FIG. 4 is plan view of the cannula of this invention.

Cannula 42, now described by reference to FIGS. 4 and 6B, includes a hub 44. Hub 44 is formed from plastic or other electrically insulating material. (Cannula hub 44 and the above the below described electrode hub 68 of FIG. 1 are aesthetically different than the hubs depicted in the other Figures.) Hub 44 is formed with a longitudinally extending outer face 41. Face 41 is formed with indicia 43 best seen in FIGS. 6A and 7A. In the depicted version of the invention, indicia 43 is shown as two linearly aligned bars. The cannula hub 44 is formed to have a through bore 46 that extends axially through the hub. Hub bore 46 is dimensioned to receive the body 74 of the electrode 62. The proximal portion of hub bore 46 is generally of constant diameter. (Here "proximal" is understood to mean towards the practitioner holding assembly 32, away from the tissue to which the assembly 32 is applied. "Distal" is understood to mean towards the tissue to which assembly 32 is applied, away from the practitioner.) Hub 44 is further shaped so that, as bore 46 extends distally forward from the constant width proximal section, the diameter of the bore decreases. At the most distal end of the hub 44, bore 46 has a diameter that allows the electrode body 44 to slide through and out of the bore.

A cannula body 50 extends distally forward from hub 44. Cannula body 50 is tube-shaped and formed from a flexible conductive material such as stainless steel. The cannula body 50 has opposed proximal and distal ends, the proximal end being the end disposed in hub 44. In many versions of the invention cannula body 50 is of size 18 gage or smaller (1.25 mm or less in outer diameter.) In still other versions of the invention, cannula body is of size 20 gage or smaller (0.9 mm or less in outer diameter). Cannula body 50 has an axially extending lumen 52. The proximal end of body 50 is mounted to the hub 44 so the proximal portion of lumen 52 is coaxial with hub bore 64. Lumen 52 extends from the proximal to the distal end of the body 50. Not identified is the distal end opening in the distal end of body 50 that opens into lumen 52. In some versions of the invention the most proximal section of body 50, including the proximal end, is heat staked or adhesively secured in cannula hub 44.

Cannula 42 is further constructed so that body 50 is not straight along the whole of the length of the body. In some versions of the invention, the body is shaped so the first 80% to 90% of the body that extends forward from hub is linear in shape. Through this portion of the body, body lumen 52 is coaxial with hub bore 46. Forward of this linear section, the cannula body is formed with a bend 54. Bend 54 has a radius of curvature of 40 to 60 mm. Forward of bend 54, cannula body has a distal section, section 56. Cannula body distal section 56 is generally linear in shape. The distal section has a length of approximately 5 to 10 mm. The cannula body 50 is further formed to a side opening 58. Side opening 58 is located on the side of the body that forms the outer surface of bend 54. The cannula body 50 is formed so that the lumen 52, in addition to extending through the proximal section of the body, also extends through bend 54 and distal section 56. Side opening 58 thus opens into the body lumen 52.

Cannula body 50 is further formed so that distal end is both open and has a flared tip 60. More particularly the tip is flared so that the most distal portion of the body is a point forward of the inner side of bend 54. The cannula 42 itself is constructed so that body 50 extends forward from the hub 44 so that portion of the body forming the inner surface of bend 54 is directed towards the face 41 of the hub on which indicia 43 is located.

A sleeve 64, seen only in FIG. 2, formed from electrically insulating material is disposed over the outer surface of the cannula body 50. The sleeve 64 extends proximally rearward from a position slightly proximal to side opening 58. The sleeve 64 extends proximally so as to extend over the portion of the cannula that is disposed in hub 44.

The electrode 66, now described by reference to FIGS. 3, 5, 6A, 6B and 7B, includes a hub 68 formed from plastic or other electrically insulating material. Hub 68 is formed to have two opposed faces 70 and 75. Face 70 is formed with a first indicia 72, shown as "I". The opposed hub face, face 75 is formed with a second indicia 76, shown as "V"

Figure 5:
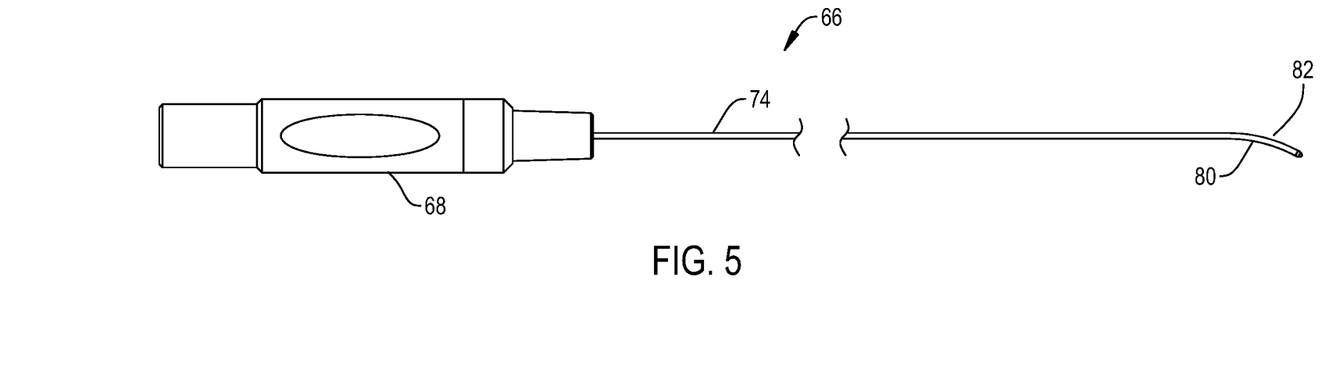
FIG. 5 is plan view of the electrode of this invention.

A tube like body 74 formed of conductive material that has both flexible and elastic characteristics extends forward from hub 68. More particularly, the material is elastic so that, when subjected to deformative strain up to 3% and in some situations up to 6% deformative strain from its initial shape, the body will not permanently deform and return to its initial shape. In one version of the invention, body 74 is formed from a nickel titanium alloy known as Nitinol. Body 74 has an overall length such that when electrode 66 is inserted in the cannula 42 so that the electrode hub 68 abuts cannula hub 44, the distal end tip of the electrode body is extends forward of at least a portion of the face forming the flared tip 60 of the cannula body 50. The distal end tip of the electrode body does not extend beyond the distalmost end of the cannula body 50. In some versions of the invention, when the electrode 66 is fully seated in the cannula 42, the distal end top of the electrode body is located approximately 0.4 to 1.4 mm rearward of the distalmost tip of the cannula body 50. The electrode body 74 has an outer diameter dimensioned so that when the electrode body 74 seats in cannula lumen 54, there is contact between the inner surface of the cannula body 50 that defines lumen 54 and the outer surface of electrode body 74.

Electrode body 74 is further designed to have a bend 80. In FIG. 5, the curvature of bend 80 is exaggerated for purposes of illustration. Bend 80 is located in the electrode body 74 so that when the electrode 66 is seated in the cannula 42, the electrode bend 80 seats in the section of the cannula lumen 52 defined by cannula bend 54. When the electrode 66 is assembled, the body 74 is placed in a rotational orientation relative to the hub 68 so that a distal section 82 of the body, the section distal to bend 64, is directed towards hub face 70. It should be further understood that the distal end of body distal section 82 is the distal end tip of the electrode 66.

Figure 6A:
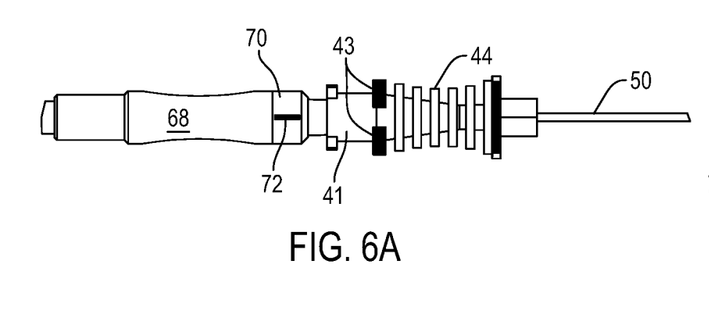
FIG. 6A is a diagrammatic depiction of the alignment of the cannula and electrode indicia of the assembly of this invention when the assembly is configured to source current from a single tip.
Figure 6B:
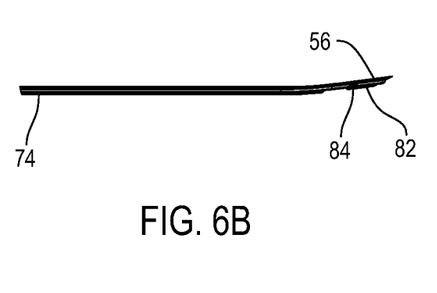
FIG. 6B is a cross sectional view of the assembly when the assembly is configured to source current from a single tip.
Figure 7A:
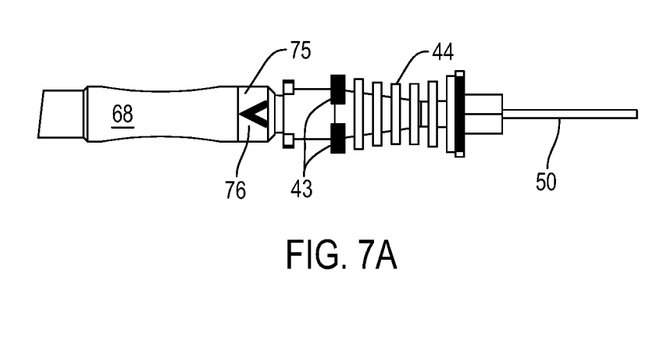
FIG. 7A is a diagrammatic depiction of the alignment of the cannula and electrode indicia of the assembly of this invention when the assembly is configured to source current from a single tip.
Figure 7B:
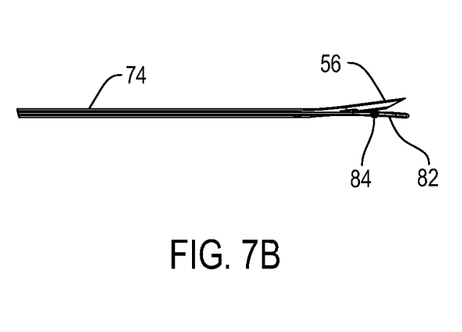
FIG. 7B is a partial cross sectional view of the assembly of this invention when the assembly is configured to source current from a single tip.

A thermocouple 84, represented by an oversized dot in FIGS. 6B and 7B is disposed in the electrode body 80. Thermocouple 84 is disposed in the body distal section 82. Insulated wires (not illustrated,) extend from the thermocouple 84 through the electrode body 75 to hub 68. The structure of the thermocouple 84 and the conductors that extend to the thermocouple are not part of the present invention.

A cable 92 (FIG. 1) extends proximally from the electrode hub 68. The cable 68 contains a wire that, through the hub, is connected to the electrode body 74. Also internal to the cable 92 are wires that connect to the wires internal to the electrode body 74 that are connected to the thermocouple 84. The proximal end of the cable 92 is connected to the control console 36.

Control console 36 includes a power supply (not illustrated) capable of sourcing a variable current to the electrode assembly 32. Ground pad 34 functions as the return conductive terminal for the power source. Typically, the current is AC current. Control console 36 is configured to allow the practitioner to adjust the frequency, current and voltage levels of the sourced current. The specific structure of the control console 36 is not part of the present invention. Features of control consoles that can be employed as control console 36 of system 30 this invention are disclosed in the incorporated by reference US Pat. Pubs. No. 2005/0267553 SYSTEM AND METHOD FOR CONTROLLING ELECTRICAL STIMULATION AND RADIOFREQUENCY OUTPUT FOR USE IN AN ELECTROSURGICAL PROCEDURE published Dec. 1, 2005 and No. 2007/0016185, MEDICAL BIPOLAR ELECTRODE ASSEMBLY WITH A CANNULA HAVING A BIPOLAR ACTIVE TIP AND A SEPARATE SUPPLY ELECTRODE AND MEDICAL MONOPOLAR ELECTRODE ASSEMBLY WITH A CANNULA HAVING A MONOPOLAR ACTIVE TIP AND A SEPARATE TEMPERATURE-TRANSDUCER POST published Jan. 18, 2007.

Electrosurgical system 30 of this invention is prepared for use by adhering the ground pad 34 to the patient. A cable 35 connects the ground pad 34 to control console 36.

Cannula 42 is inserted into the patient adjacent the subcutaneous tissue that is to be subjected to the ablation process. In the insertion process the flared distal end tip 60 of the cannula is the portion of the electrode assembly 32 that punctures the skin. In this step, electrode 66 is not fitted to the cannula 42. Instead, a flexible stylet (not illustrated) is seated in the cannula lumen 52. The stylet inhibits the cannula body 50 from bending to the extent that such bending results in the permanent deformation of the cannula.

The practitioner steers the cannula 42 so it is located in the vicinity of the target tissue, the tissue that is to be subject to the ablation procedure. Owing to its relatively small diameter of the cannula body 50, the cannula is relatively flexible. This flexibility facilitates the ability of the practitioner to steer the cannula to the vicinity of the target tissue. As part of this steering process, the practitioner positions the cannula so it is in the proper orientation relative to the tissue to be ablated. Once the cannula is properly positioned, the stylet is removed.

The practitioner then inserts the electrode 66 in the cannula 42. If the particular procedure only requires the sourcing of current through a small volume of tissue adjacent the distal end of the assembly 32, the electrode is seated so as to position the distal section 82 of the electrode body 74 in the cannula body distal section 56 as seen in FIG. 6B. The practitioner so seats the electrode by setting the rotation orientation of the electrode body 74 inside the cannula body 50 so that cannula and electrode bends 54 and 80, respectively, extend in the same direction. The practitioner sets this orientation of the electrode by aligning the electrode hub 68 so that as the hub 68 is moved towards cannula hub 42, electrode indicia 72 faces cannula indicia 43 as seen in FIG. 6A.

As a consequence of the electrode 66 being so oriented, when the distal section 84 of the electrode body approaches the cannula bend 54, the electrode bend 80 causes the electrode distal section 82 to curve into the cannula body distal section 56. At the end of this insertion process, the distal end tip of the electrode body 74 is depicted in FIG. 6B, seated inside the distalmost portion of cannula lumen 52. When the assembly 50 is in this configuration, configuration, current is source from just one active tip, the insulation free portion of the cannula body 50; bend 54 and distal section 56.

Alternatively, the practitioner may want to flow current through a relatively large volume of tissue adjacent the distal end of the assembly 32. To perform this type of procedure, the practitioner seats the electrode 66 so the distal section 82 extends out of cannula body side opening 58. Electrode 66 is so positioned by orientating the electrode body in the cannula so that along the longitudinal axis of the cannula proximal section, the electrode bend 80 has an orientation that is opposite to that of cannula bend 54. Electrode 66 is so oriented by rotating the electrode so electrode indicia 76 is placed in orientation with cannula indicia 43 as seen in FIG. 7A. Once the electrode 66 is so orientated, the electrode body 74 is advanced through the cannula lumen 52. Eventually the distal end tip of the electrode body 74 reaches cannula side opening 58. Owing the elastic characteristics of the material forming the electrode body 74, the potential energy stored in bend 80 is released. This energy forces the body distal section 82 out of the cannula body side opening 58. When the electrode is fully seated in the cannula, the distal section 82 of the electrode body 74 is located outside of and adjacent to the cannula distal section 56 as seen in FIGS. 2, 3 and 7B.

When current is sourced through assembly as seen in FIG. 7B, the current is thus sourced through two active tips; the exposed bend and distal section of the cannula body and the exposed distal section 82 of the electrode body. The current thus flows through a larger volume of tissue immediately adjacent the cannula than when the assembly is configured to source current from a single active tip.

The cannula and electrode of this assembly can thus be configured to operate in one of two modes, a mode in which the assembly sources current out of a single active tip or a mode in which the assembly sources current out of plural active tips. This allows the practitioner to, by setting the mode of operating of the assembly, set if the current is flowed through a relatively small volume or relative large volume of tissue adjacent the assembly 32.

Further, regardless of the mode of operation the electrode 66 is typically fully seated in the cannula 42. Consequently, regardless of the operating mode, the thermocouple 84 is spaced essentially the same distance from tissue through which the current is flowed. The added separation of the thermocouple from the tissue when the electrode distal section 56 of cannula body 50 is minimal. Thus, in either mode of operation, the signal output by the thermocouple 84 representative of tissue temperature, represents the actual temperature of the tissue with the same degree of accuracy. This is useful because a practitioner may want to set the control console to cause a current to be applied to the tissue that ensures that the tissue is heated to a specific temperature. When the system 30 is so configured, the control console 36 employs the output signal from the thermocouple as the signal representative of tissue temperature.

It is a still further feature of this invention is that, once the cannula 42 is inserted in the patient, the practitioner may reset the mode of operation of the assembly 32. For example, the practitioner may start the procedure by sourcing current from just the single active tip, cannula body distal section 56. The practitioner can then reset the assembly so that the current is formed from both tips, the cannula body distal section and the electrode body distal section. The practitioner performs this switch by first partially withdrawing the electrode body 74 from the cannula lumen 52. The electrode 66 is then rotated to place electrode indicia 76 is placed in registration of cannula indicia 43. The electrode body 74 is then fully reinserted in the cannula lumen 52. This rotation and reinsertion of the electrode body 74 results in the extension of the electrode body distal section out of the cannula body side opening 58. The assembly is then ready for operation in the mode in which the current is sourced from the two active tips.

Using the technique opposite from which is described above, assembly 32 once fitted to the patient can be switch from the plural active tip operating mode to the single active tip operating mode.

The above is directed to one specific version of the invention. Other versions of the invention may have features different from what has been described.

For example, there is no requirement that in all versions of the invention a thermocouple be the component disposed in the electrode that provides a signal representative of temperature. A thermal resistor or other temperature sensitive transducer may perform this function.

Likewise there is no requirement that in all versions of the invention either the cannula body or electrode body be components formed out of a single section of material. For example, the cannula body may include a proximal section formed from a nonconductive plastic. The bend and the distal section may be formed from metal or another conductive material.

Further the described cannula is what is referred to as a monopolar cannula. The cannula has a single conductive surface. In an alternative version of this invention, the cannula may be a bipolar cannula. This type of cannula has two conductive surfaces that are electrically insulated from each other. The assembly of this version of the invention is used to perform what is known as a bipolar ablation procedure. The cannula second conductive surface functions as the return conductive terminal.

In this version of the invention, when the assembly is operated in the plural active tip mode, the exposed distal section 82 of the electrode 66 and one of the exposed sections of the cannula form a pair of common active tips. The second exposed section of the cannula serves as the return conductive terminal.

Likewise the electrode body may be formed from plural sections of different material. For example the electrode body may have a proximal section formed from an elastic plastic. This plastic portion of the electrode body may be formed with the flexible bend. Distal to bend, the electrode may have a tip formed from a relatively inflexible conductor. An advantage of this version of the is that when the assembly is configured to operate in the plural active tip mode and the electrode is deployed out of the cannula side opening, the relatively inflexible exposed distal end may be less prone to breakage.

Further, there is no limitation that the invention solely be used in what are referred to as a monopolar procedure, a procedure in which the ground pad functions as the return electrode. Assembly 32 of this invention may be used to perform what is referred to as a parallel bipolar ablation procedure. In this type of procedure two cannula and electrode assemblies are inserted in the patient. These assemblies are positioned on opposed sides of the tissue through which the current is to be flowed. In this type of procedure, the second cannula and electrode assembly serves as what is referred to as the return electrode.

In these types of procedure, there is no requirement that both cannula and electrode assemblies be of the type of this invention. In this type of procedure it is recommended that the assembly 32 of this invention be orientated so that the electrode bend 80 is positioned so that the electrode distal section 82 be directed towards the tissue through which the current is to be filed. This recommendation applies when the assembly 32 is operated either the single or active tip mode or the plural active tip mode. This orientation of the electrode 66 is suggested to ensure that the thermocouple 84 is positioned relatively close to the tissue through which the current is to be flowed. This increases the extent to which the thermocouple outputs a signal that, as closely as possible, represents the temperature of the tissue through which the current is flowed.

Figure 8:
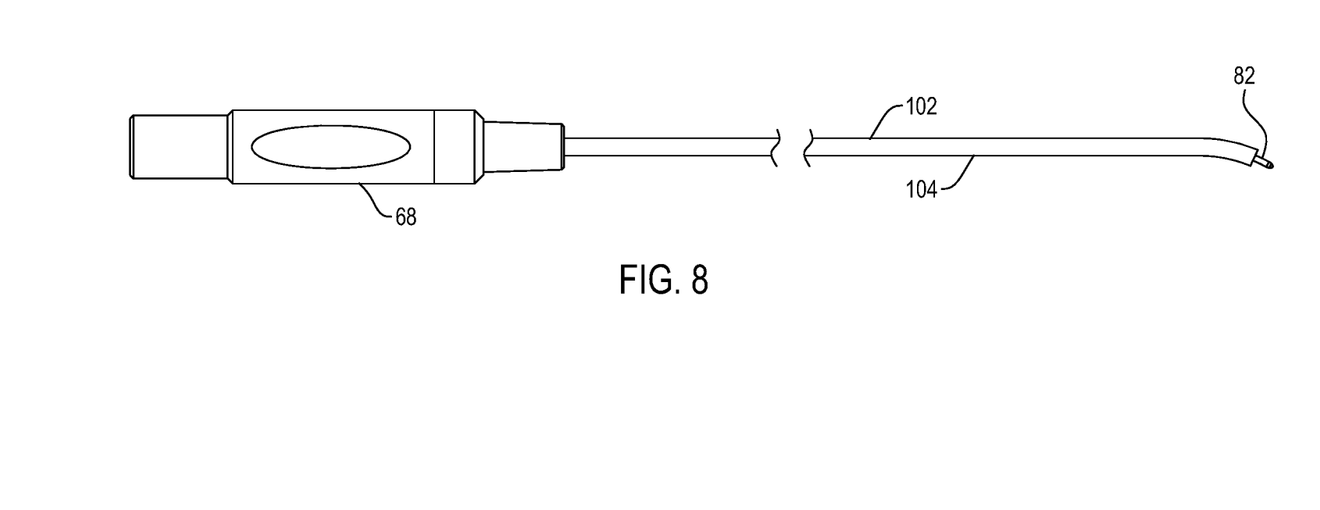
FIG. 8 is a plan view of an alternative electrode of this invention.

FIG. 8 illustrates an alternative electrode 102 of this invention. Electrode 102 includes the same features of initially described electrode 66. The electrode 102 further includes a sleeve 104 formed from electrically insulating material that is disposed over the electrode body 74. Sleeve 104 extends distally from hub 68 to a location forward of the bend 80. In FIG. 8, the wall thickness of sleeve 104 is exaggerated for purposes of illustration.

The electrode of FIG. 8 is used in versions of this invention wherein a separate set of conductors extends from cannula hub 44 to the control console 36. These conductors (not illustrated) provide an electrical connection between the control console 36 and the cannula body 50.

The cannula-and-electrode assembly of this invention can be thus operated as either a monopolar unit or a standalone bipolar unit. The assembly is operated as a monopolar unit by seating electrode 102 in cannula 44 so that the electrode body distal section 82 seats in cannula body distal section 56. When the assembly is operated in this state, there is only a need to connect the electrode 102 to the control console 36. The assembly in this state is operating with a single active tip; the insulation free portion of the electrode distal section 82. Ground pad 34 functions as the return terminal.

Alternatively, the practitioner may want to operate the assembly is a standalone bipolar unit. The assembly is so configured by orientating electrode 102 so that when the body is inserted in the cannula lumen 52, the electrode body distal section protrudes out of cannula side opening 58. It should be understood that when the electrode 102 is so positioned, the distal most portion of sleeve 104 also protrudes out of the cannula side opening 58. Thus when the assembly is so configured, the cannula body distal section 56 and the electrode body distal section 82 are electrically insulated from each other. To operate the assembly in this configuration, it is further necessary to connect the cable that extends from the cannula hub 44 to the control console 36.

To operate the assembly in this configuration, current is flowed from the console power supply through the cannula. The exposed cannula body distal section 56, which is one of the active tip, functions as the active tip. The exposed electrode body distal section 82 functions as the return terminal. By so configuring the assembly of this invention, the practitioner can if desired, flow current through the small volume of tissue that surrounds the exposed tips.

An alternative embodiment of this version of the invention can be formed by provide the cannula with a liner that extends around the interior wall of the body that defines lumen 52. This linear also cover the outer surface of the cannula that defines side opening 52.

Accordingly, it is an object of the appended claims to cover all such modifications and variations that come within the true spirit and scope of this invention.

What is claimed is:

1. An assembly for radiofrequency ablation of tissue, said assembly comprising: a cannula comprising: a cannula hub comprising indicia; a cannula body comprising a cannula proximal section including a cannula proximal end coupled to said cannula hub, a cannula distal section including a cannula distal end opposite said cannula proximal end with said cannula distal section comprising electrically conductive material for ablating the tissue, a cannula bend between said cannula proximal and distal sections and defining an innerside of said cannula body in a direction of said cannula bend and an outer side of said cannula body opposite said innerside, a lumen extending between said cannula proximal and distal ends, and a side opening in communication with said lumen and radially disposed on said outer side of said cannula body and axially disposed on said cannula bend; an electrode comprising: an electrode hub comprising a first indicia and a second indicia; and an electrode body comprising an electrode body proximal section including an electrode body proximal end, an electrode body distal section including an electrode body distal end opposite said electrode body proximal end, and an electrode body bend located between said electrode body proximal and distal ends, wherein said electrode body is coupled to said electrode hub and dimensioned to be inserted within said lumen of said cannula body in a first rotational orientation in which said first indicia on said electrode hub is in registration with said indicia on said cannula hub, said electrode body bend is in a same orientation as said cannula bend, and said electrode body distal section of said electrode body is seated within said cannula distal section, and further insertable within said lumen of said cannula body in a second rotational orientation in which said second indicia on said electrode hub is in registration with said indicia on said cannula hub, said electrode body bend is out of orientation with said cannula bend, and said electrode body distal section extends through said side opening of said cannula body.

2. The assembly of claim 1, wherein said electrode hub comprises opposing faces with said first indicia disposed on one of said opposing faces and said second indicia disposed on another one of said opposing faces.

3. The assembly of claim 1, wherein said cannula hub comprises a face with said indicia of said cannula hub disposed on said face with said indicia indicative of an orientation of said cannula distal section relative to said cannula proximal section from said cannula bend.

4. The assembly of claim 1, wherein said electrode body comprises a length defined between said electrode body proximal and distal ends with said length being substantially equal to a length of said cannula body defined between said cannula proximal and distal ends such that when said electrode body is inserted within said cannula body in said first rotational orientation, said electrode hub abuts said cannula hub and said electrode distal end is seated within said cannula distal section proximate said cannula distal end.

5. The assembly of claim 1, wherein said cannula body is formed from a single piece of material.

6. The assembly of claim 1, wherein said electrode body is formed from a single piece of material.

7. The assembly of claim 1, wherein said electrode body further comprises an elastic section formed from a nickel titanium alloy.

8. The assembly of claim 1, further comprising an electrically insulating sleeve disposed over said cannula body with said electrically insulating sleeve including an end that terminates at a position proximal to said side opening.

9. The assembly of claim 1, further comprising a temperature sensor disposed on said electrode body distal section.

10. The assembly of claim 1, wherein said assembly is configured to be operated as a monopolar cannula and electrode assembly in which said electrode body distal section extends through said side opening of said cannula body and is not electrically insulated from said cannula distal section.

11. The assembly of claim 1, further comprising a tip at said cannula distal end with said tip flared to a point on said inner side of said cannula body opposite said outer side.

12. An assembly for radio frequency ablation of tissue, said assembly comprising: a cannula comprising: a cannula hub comprising indicia; a cannula body comprising a cannula proximal section including a cannula proximal end coupled to said cannula hub, a cannula distal section including a cannula distal end opposite said cannula proximal end with said cannula distal section comprising electrically conductive material for the ablation of the tissue, a cannula bend between said cannula proximal and distal sections and defining an innerside of said cannula body in a direction of said cannula bend and an outer side of said cannula body opposite said innerside, wherein said indicia of said cannula hub indicative of an orientation of said cannula distal section relative to said cannula proximal section from said cannula bend, a lumen extending between said cannula proximal and distal ends, and a side opening in communication with said lumen and radially disposed on said outer side of said cannula body and axially disposed on said cannula bend; an electrode comprising: an electrode hub comprising a first indicia and a second indicia; and an electrode body coupled to said electrode hub and dimensioned to be inserted and seated within said lumen of said cannula body with said electrode body comprising an electrode body proximal section including an electrode body proximal end, an electrode body distal section including an electrode body distal end opposite said electrode body proximal end, and an electrode body bend located between said electrode body proximal and distal sections, wherein said first and second indicia of said electrode hub are indicative of an orientation of said electrode body distal section relative to said electrode body proximal section from said electrode body bend, wherein said indicia of said cannula hub and said first and second indicia of said electrode hub are arranged such that, when said first indicia of said electrode hub is placed in registration with said indicia of said cannula hub as said electrode body is being inserted within said lumen of said cannula body, said electrode body bend is in a same orientation as said cannula bend and said electrode body distal section extends past said side opening of said cannula body to be seated within said lumen of said cannula distal section, and further arranged such that, when said second indicia of said electrode hub is placed in registration with said indicia of said cannula hub as said electrode body is being inserted within said lumen of said cannula body, said electrode body bend is out of orientation with said cannula bend and said electrode body distal section extends through side opening of said cannula body.

13. The assembly of claim 12, wherein said electrode body bend is formed from elastic material such that, when said electrode body distal section is seated within said lumen of said cannula distal section, said electrode body bend is aligned with said cannula bend.

14. The assembly of claim 12, wherein said electrode hub further comprises opposing faces with said first indicia disposed on one of said opposing faces and said second indicia disposed on another one of said opposing faces.

15. A method of performing radiofrequency ablation of tissue with a source of radiofrequency energy and an assembly, the assembly including a flexible stylet, a cannula having cannula hub including indicia and a cannula body coupled to the cannula hub and defining a lumen and a side opening in communication with said lumen and radially disposed on an outer side of a cannula bend, wherein the cannula bend defines an inner side of said cannula body in a direction of said cannula bend, the outer side of the cannula bend is disposed opposite the innerside, and the side opening is proximal to a cannula distal section including electrically conductive material for ablating the tissue, and an electrode having an electrode hub including a first indicia, a second indicia, and an electrode body coupled to the electrode hub and including an electrode bend proximal to an electrode distal section including electrically conductive material for ablating the tissue, said method comprising the steps of: directing the cannula body with the flexible stylet seated in the lumen of the cannula body through overlying skin such that the cannula distal section is positioned adjacent the tissue; removing the flexible stylet from the lumen of the cannula body; inserting the electrode into the lumen of the cannula body with the electrode distal section positioned proximal to the side opening of the cannula body; orienting the electrode body relative to the cannula body o place the second indicia of the electrode hub in registration with the indicia of the cannula hub such that the electrode bend is out of orientation with the cannula bend; advancing the electrode relative to the cannula body such that the electrode distal section extends through the side opening of the cannula body; operating the source of radiofrequency energy with the assembly in a dual active tip mode in which the electrode distal section is extending through the side opening and the radiofrequency energy is provided to the electrically conductive material of each of the cannula distal section and the electrode distal section to ablate the tissue; after the step of advancing, at least partially withdrawing the electrode body relative to the cannula body to position the electrode distal section proximal to the side opening of the cannula body; reorienting the electrode body relative to the cannula body to place the first indicia of the electrode hub in registration with the indicia of the cannula hub such that the electrode bend is in a same orientation as the cannula bend; and advancing the electrode body relative to the cannula body such that the electrode distal section extends past the side opening of the cannula body to be seated within the cannula distal section.

16. The method of claim 15, further comprising operating the source of radiofrequency energy with the assembly in a single active tip mode in which the electrode distal section is seated within the cannula distal section and the radiofrequency energy is provided between the electrically conductive material of each of the cannula distal section and the electrode distal section to ablate the tissue.

17. The method of claim 15, wherein the step of operating the source of radiofrequency energy with the assembly in the dual active tip mode further comprises operating the source of radiofrequency energy with the assembly as a monopolar assembly in which the electrically conductive material of each of the cannula distal section and the electrode distal section are not electrically insulated from one another in order to ablate a larger volume of the tissue.

* * * * *